United States Patent [19]

Crowninshield

[11] Patent Number: 5,554,192
[45] Date of Patent: Sep. 10, 1996

[54] INTRAMEDULLARY IMPLANT STEM AND CENTRALIZER

[75] Inventor: Roy D. Crowninshield, Warsaw, Ind.

[73] Assignee: Zimmer, Inc., Warsaw, Ind.

[21] Appl. No.: 317,697

[22] Filed: Oct. 5, 1994

[51] Int. Cl.[6] ........................................... A61F 2/28
[52] U.S. Cl. .................. 623/16; 623/20; 623/22
[58] Field of Search .................. 623/16, 17, 18, 623/19, 20, 23

[56] References Cited

U.S. PATENT DOCUMENTS

| | | |
|---|---|---|
| D. 339,865 | 9/1993 | Geremakis et al. . |
| 3,793,650 | 2/1974 | Ling et al. . |
| 4,268,920 | 5/1981 | Engelbrecht et al. . |
| 4,623,353 | 11/1986 | Buechel et al. ............................ 623/23 |
| 5,080,680 | 1/1992 | Mikhail ...................................... 623/23 |
| 5,108,439 | 4/1992 | Morscher et al. . |
| 5,507,831 | 4/1996 | Burke ........................................ 623/16 |

FOREIGN PATENT DOCUMENTS

| | | | |
|---|---|---|---|
| 0050533B1 | 4/1982 | European Pat. Off. . | |
| 2683992 | 5/1993 | France ....................................... 623/23 |
| 2104391B | 3/1983 | United Kingdom . | |

OTHER PUBLICATIONS

Richards Modular Hip System Brochure—Design Advantages—No date available.
Zimmer, Inc.—Harris Precoat Plus Hip Prosthesis—Lit No. 97–9028–01, 1988.

*Primary Examiner*—Robert A. H. Clarke
*Attorney, Agent, or Firm*—Margaret L. Geringer

[57] ABSTRACT

An implant stem 10 and distal centralizer 20. Implant stem 10 has a plurality of longitudinal channels 14 formed around its periphery adjacent its distal end 12. Channels 14 converge radially toward the apex of the stem distal end 12. Channels extend only partially into the body of implant stem 10 to provide sufficient material to maintain the structural integrity of the distal end of the implant. Centralizer 20 includes a plurality of radially extending blades 22. The proximal end of each blade 22 is shaped to extend upwardly for securely mating with implant stem 10. The complimentary cruciate configuration of channels 14 and blades 22 allows centralizer 20 to be securely attached to implant stem 10.

10 Claims, 2 Drawing Sheets

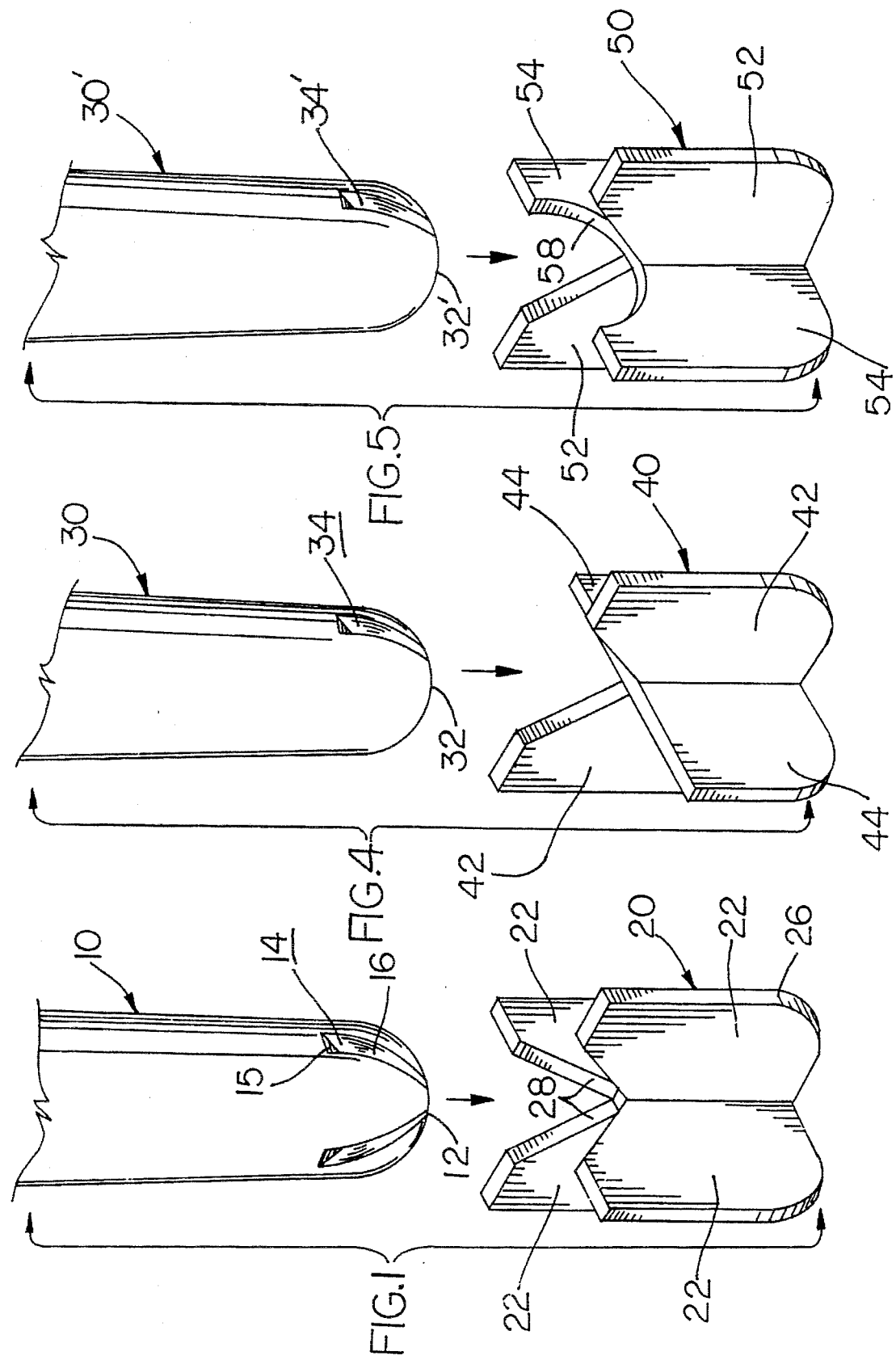

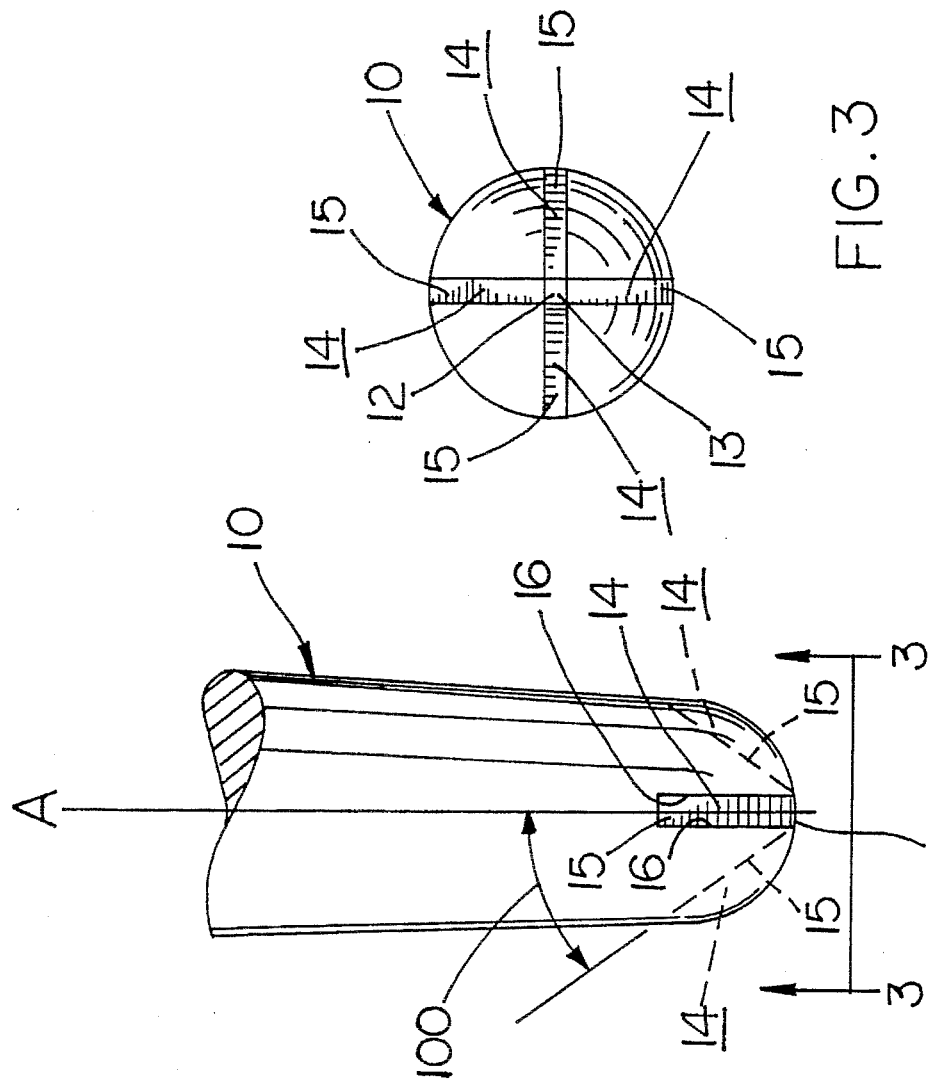

5,554,192

INTRAMEDULLARY IMPLANT STEM AND CENTRALIZER

This invention relates to an implant prosthesis and in particular an implant prosthesis including an intramedullary implant stem and a distal centralizer.

BACKGROUND OF THE INVENTION

In joint prostheses, centering devices or centralizers are used to position an implant stem, particularly femoral implant stems, within an operatively prepared intramedullary cavity. The centralizers position the implant stem so that the stem can be implanted into a bed of bone cement with a uniform thickness of cement surrounding its circumference. Often, a centralizer is used at both the proximal and distal ends of an implant stem. Centering devices are well known and have been developed in a variety of shapes and configurations. Typically, distal centralizers are configured to include a plurality of edges, barbs, or blades that press against or embed in the bone wall as the implant is driven into the intramedullary cavity. Generally, distal centralizers are attached to an implant stem by a post which is inserted or threaded into a bore formed in the stem's distal end, or by an opening in the centralizer which fits about the distal end of the stem. With implant stems which include a bore to receive a distal centralizer with a corresponding post, the bore does not typically fill with cement in the instance when a surgeon elects not to utilize the centralizer. An air bubble may thus expand into the cement creating a defect in the cement mantle. Accordingly, a filler peg is typically provided to fill the hole in the instance where the distal centralizer is not utilized.

Smith & Nephew Richard Inc. of Tennessee has developed an implant stem and distal centralizer that are connected using a tapered fit between the blades of the distal centralizer and the implant stem. The implant stem has two cross slots formed through the distal end of the stem in a cruciate configuration. The slots extend transversely across the width of the implant stem. The distal centralizer includes four blades which extend radially in a "plus sign" shaped configuration. The configuration of the blades allows the centralizer to be seated within the cross slots of the implant stem. In the instance where the surgeon elects not to utilize this distal centralizer, the transversely extending cross slots could provide a chance for an air bubble to form, if the cement does not fill the slots, which would not be desirable.

SUMMARY OF THE INVENTION

The implant stem and distal centralizer of this invention provide a stable connection while maintaining the structural integrity of the implant stem. The centralizer is attached to the implant stem by a plurality of blades which are press fit into a plurality of longitudinal grooves or channels formed in the implant stem's distal end. The channels extend only partially into the body of the implant stem to provide sufficient material to maintain the structural integrity of the distal end of the implant.

In the preferred embodiment, the implant stem has four longitudinal grooves or channels formed in its distal end. The channels are equally spaced around the circumference of the implant stem in a complimentary cruciate configuration and converge radially towards the apex of the stem's distal end. The centralizer includes four blades which extend radially in a cruciate configuration. The proximal end of each blade is shaped to extend upwardly toward the stem's distal end and has an oblique inner edge, which allows each blade to be securely seated within one of the longitudinal channels formed in the implant stem. The side walls of each channel are tapered slightly to facilitate a press fit connection between the centralizer and implant.

In two alternative embodiments, only two channels are formed in the implant stem; consequently, the configuration of the centralizers is modified slightly so that only two blades are used to secure the centralizer. In the second embodiment, the centralizer includes two pair of blades. One pair of blades is configured to be seated within the channels formed in the implant stem. The other pair of blades is shortened so as to not contact the distal end of the implant stem. In the third embodiment, the centralizer again includes two pair of blades. One pair of blades is configured to engage within the channels. The other pair of blades has an arcuate inner edge, which conforms to the exterior contour of the distal end of the implant stem. When the centralizer is connected, these blades abut against the outer surface of the implant stem to provide additional support.

Accordingly, an advantage of this invention is to provide for an implant stem and distal centralizer which can be securely connected while preserving the structural integrity of the components.

Another advantage is to provide for an implant stem and centralizer which are easy and cost effective to manufacture.

A further advantage of the present invention is to provide at least two channels (or at least one pair of channels) which converge toward the apex of the stem. Due to the angle of the oblique inner wall of the channels, cement is able to flow up into and fill the channels if the surgeon elects not to utilize the corresponding distal centralizer. In addition, the converging channels progressively lessens the bending stiffness of the stem which reduces stress concentration in the cement at the distal tip.

Other advantages will become apparent upon a reading of the following description.

BRIEF DESCRIPTION OF THE DRAWINGS

A preferred embodiment of the invention has been depicted for illustrative purposes only wherein:

FIG. 1 is a perspective view of one embodiment of the distal end of the implant stem and the distal centralizer of this invention;

FIG. 2 is a side view of the implant stem of FIG. 1;

FIG. 3 is a bottom view of the stem taken at lines 3—3 of FIG. 2;

FIG. 4 is a perspective view of a second embodiment of the distal end of the implant stem and distal centralizer of this invention; and FIG. 5 is a perspective view of a third embodiment of the distal end of the implant stem and distal centralizer of this invention.

DESCRIPTION OF THE PREFERRED EMBODIMENT

The preferred embodiments herein described are not intended to be exhaustive or to limit the invention to the precise form disclosed. They are chosen and described to explain the principles of the invention and its application and practical use to enable others skilled in the art to utilize its teachings.

Intramedullary implant stems and distal centering devices or centralizers are well known in the art. The embodiments described herein illustrate complimentary configurations between the implant stems and centralizers. The teaching of this invention can be incorporated into any intramedullary implant stem which uses or incorporates a distal centering device. Although a cruciate configuration is predominate in the embodiments described below, any mating configuration can be used. For example, three or five or more blades (not shown), rather than four, could be readily utilized with the present invention.

FIGS. 1, 2 and 3 show the preferred embodiment of the distal end 12 of an implant stem 10 and a distal centralizer 20. As shown, the rounded distal end 12 of an implant stem 10 has four longitudinal grooves or channels 14. Channels 14 are equally spaced around the circumference of implant stem 10 in a cruciate configuration. The cross section of each channel 14 is defined by an oblique inner wall 15 and two side walls 16. The oblique inner wall 15 is at an angle 100 relative to the longitudinal axis A of stem 10. Angle 100 may suitably be in the range of about 20° to 45° with about 30° being preferable, although any suitable angle may be utilized. As shown in FIGS. 2 and 3, channels 14 defined in implant stem 10 converge radially and equiannularly towards the apex 13 of distal end 12 from a mid point along the body of implant stem 10. It should be noted that channels 14 extend only partially into the body of implant stem 10 to provide sufficient material to maintain the structural integrity of the distal end of the implant stem. It is noted that the oblique inner walls 15 may intersect each other (not shown) toward the apex 13 of the distal end 12 of the stem 10 to enable the centralizer to be slightly recessed into the distal end 12.

As shown in FIG. 1, centralizer 20 includes four flat blades 22 which extend radially in a cruciate configuration. The width of each blade 22 is substantially equal to the width of channels 14. The proximal end of each blade 22 is shaped to extend upwardly for securely mating with distal end 12 and has an oblique inner edge 28. The angle of inner wall 15 is complimentary to the angle of inner edge 28 of blades 22. Each blade 22 has an exterior edge 26 which is contoured to engage the bone wall of the intramedullary cavity.

The complimentary cruciate configuration of channels 14 and blades 22 allows centralizer 20 to be securely attached to implant stem 10. When centralizer 20 and implant stem 10 are connected, the inner edge 28 of each blade 22 lies flat against inner wall 15 of each channel 14 and the sides of blades 22 are fitted between side walls 16. Side walls 16 of channels 14 are tapered slightly to facilitate the press fit connection with blades 22.

FIGS. 4 and 5 show two alternative embodiments of this invention. In both alternative embodiments, the implant stem 30 has only two channels 34 formed in its distal ends 32. As in the foregoing preferred embodiment, the channels are formed to receive the blades of the centralizer in a press fit engagement; however, the configuration of the centralizers are modified so that only two of their four blades are used to secure the centralizer. In the second embodiment (FIG. 4), centralizer 40 includes two pair of blades 42, 44. One pair of blades 42 is configured to engage within the channels of the implant stem. The other pair of blades 44 is longitudinally shortened so as to not contact the distal end 32 of the implant stem. In the third embodiment (FIG. 5), centralizer 50 again includes two pair of blades 52, 54. One pair of blades 52 is configured to engage within channels 34'. The other pair of blades 54 has an arcuate inner edge 58, which conforms substantially to the exterior contour of distal end 32' of the implant stem 30'. When centralizer 50 is connected, blades 54 abut against the outer surface of distal end 32' to provide additional support, and blades 52 are securely seated within channels 34'.

The centralizer 20, 40, 50 of the present invention may be made out of an acrylic material such as polymethyl methacrylate (PMMA), although any suitable materials may be utilized. The stem component 10, 30, 30' may be made out of a metal such as a titanium or cobalt chrome alloy, although any suitable materials may be utilized.

It is understood that the above description does not limit the invention to the details given, but may be modified within the scope of the following claims.

I claim:

1. In combination, an implant prosthesis for insertion into a cavity prepared in a bone comprising a stem component having a distal end; and a centralizer for attachment to said stem component distal end, said stem component having a plurality of longitudinal channels formed around its periphery adjacent its said distal end, said centralizer including a plurality of blade parts for engaging said stem component within said channels when said centralizer is attached to said stem component, wherein said channels each have an inner wall, which converges radially toward the apex of said stem component distal end.

2. The combination of claim 1 wherein each said channel is defined by one of the inner walls and a pair of side walls, each of the inner walls being at an oblique angle to a longitudinal axis of the stem, and wherein said pair of side walls engage one of said blade parts when said centralizer is secured to said stem component.

3. The combination of claim 2 wherein the oblique angle is about 20° to 45° to the longitudinal axis of the stem component.

4. The combination of claim 1 wherein each blade part includes a proximal end shaped to extend towards said stem component distal end and having an edge for restrictive engagement with said stem component within a said channel when said centralizer is attached to said stem.

5. The combination of claim 1 wherein the plurality of blade parts comprises at least two centralizing blades for engaging said stem component within said channels, and wherein said centralizer includes at least one additional centralizing blade positioned about said centralizer to assist in centralizing said stem component within the cavity of the bone.

6. The combination of claim 5 wherein the at least one additional centralizing blade also engages said stem component within said channels.

7. In combination, an implant prosthesis for insertion into a cavity prepared in a bone comprising a stem component having a distal end; and a centralizer for attachment to said stem component distal end, said stem component having a plurality of longitudinal channels formed around its periphery adjacent its said distal end, said centralizer including a plurality of blade parts for engaging said stem component within said channels when said centralizer is attached to said stem component, wherein said channels converge radially toward the apex of said stem component distal end, and wherein each blade part includes a proximal end shaped to extend towards said stem component distal end and having an edge for restrictive engagement with said stem component within a said channel when said centralizer is attached to said stem, and wherein the proximal end of each blade part has an oblique inner edge for mating with a corresponding oblique inner wall of a corresponding channel.

8. In combination, an implant prosthesis for insertion into a cavity prepared in a bone comprising a stem component having a distal end; and a centralizer for attachment to said stem component distal end, said stem component having a plurality of longitudinal channels formed around its periphery adjacent its said distal end, said centralizer including a plurality of blade parts for engaging said stem component within said channels when said centralizer is attached to said stem component, wherein said channels converge radially toward the apex of said stem component distal end, and wherein said plurality of blade parts comprises a first pair of blades for engaging said stem component within said channels, and wherein said centralizer further includes a second pair of blades which do not engage any of said channels.

9. The combination of claim 8 wherein said second pair of blades includes an arcuate inner edge which conforms substantially to an exterior contour of said distal end and which abut said exterior contour to provide additional support when said centralizer is attached to said stem component.

10. In combination, an implant prosthesis for insertion into a cavity prepared in a bone comprising a stem component having a distal end; and a centralizer for attachment to said stem component distal end, said stem component having a plurality of longitudinal channels formed around its periphery adjacent its said distal end, said centralizer including a plurality of blade parts for engaging said stem component within said channels when said centralizer is attached to said stem component, wherein said channels converge radially toward the apex of said stem component distal end, and wherein the plurality of blade parts comprises at least two centralizing blades for engaging said stem component within said channels, and wherein said centralizer includes at least one additional centralizing blade positioned about said centralizer to assist in centralizing said stem component within the cavity of the bone, and wherein the at least one additional centralizing blade does not engage any of said channels and includes an arcuate inner edge which conforms substantially to an exterior contour of said distal end and which abuts said exterior contour to provide additional support when said centralizer is attached to said component.

* * * * *